United States Patent
Hruza et al.

(10) Patent No.: US 10,066,881 B2
(45) Date of Patent: Sep. 4, 2018

(54) STANDING GASKET FOR HEAT EXCHANGER

(71) Applicant: Hanon Systems, Daejeon (KR)

(72) Inventors: Hynek Hruza, Nový Jičín (CZ); Keith Wilkins, Chelmsford (GB)

(73) Assignee: HANON SYSTEMS, Daejeon (KR)

(*) Notice: Subject to any disclaimer, the term of this patent is extended or adjusted under 35 U.S.C. 154(b) by 0 days.

(21) Appl. No.: 15/397,825

(22) Filed: Jan. 4, 2017

(65) Prior Publication Data

US 2017/0191764 A1    Jul. 6, 2017

(51) Int. Cl.
| | |
|---|---|
| *F16J 15/02* | (2006.01) |
| *F28F 9/02* | (2006.01) |
| *F16J 15/06* | (2006.01) |

(52) U.S. Cl.
CPC ........... *F28F 9/0226* (2013.01); *F16J 15/061* (2013.01)

(58) Field of Classification Search
CPC ......... F28F 9/0226; F16J 15/10; F16J 15/104; F16J 15/106
See application file for complete search history.

(56) References Cited

U.S. PATENT DOCUMENTS

| | | | | |
|---|---|---|---|---|
| 5,031,924 A | * | 7/1991 | Beatenbough | F16J 15/061 165/173 |
| 6,644,385 B2 | * | 11/2003 | Boissele | F28F 9/0226 165/173 |
| 6,722,660 B2 | * | 4/2004 | Gernand | F16J 15/061 277/591 |
| 6,981,704 B2 | * | 1/2006 | Okazaki | F16J 15/061 277/638 |
| 7,938,406 B2 | * | 5/2011 | Matsumoto | F02F 11/007 277/596 |
| 2011/0193298 A1 | * | 8/2011 | Yoshitsune | F16J 15/061 277/648 |

FOREIGN PATENT DOCUMENTS

EP          1921413 A1    5/2008

* cited by examiner

*Primary Examiner* — Gilbert Y Lee
(74) *Attorney, Agent, or Firm* — Schumaker, Loop & Kendrick, LLP; James D. Miller

(57) ABSTRACT

A sealing element for a heat exchanger is defined by an elongate main body. An aspect ratio of the main body is greater than 1:1, wherein a height of the main body is greater than a width of the main body. The sealing element includes a plurality of enlarged portions spaced at predetermined intervals along a length of the main body. The enlarged portions have a width greater than the width of the main body, and are laterally offset inwardly with respect to the main body. The sealing element further includes a plurality of lugs protruding laterally from the main body. First pairs of the lugs are alternatingly arranged with the enlarged portions of the sealing element. Second pairs of the lugs are spaced along ends of the sealing element. Single ones of the lugs also protrude laterally outwardly from the enlarged portions.

18 Claims, 5 Drawing Sheets

STANDING GASKET FOR HEAT EXCHANGER

CROSS-REFERENCE TO RELATED APPLICATIONS

This application claims priority to Czech Patent Application No. PV 2016-2 filed on Jan. 5, 2016, hereby incorporated herein by reference in its entirety

FIELD OF THE INVENTION

The invention relates to a sealing element for a motor vehicle, and more particularly, to a standing sealing element for a heat exchanger of a motor vehicle.

BACKGROUND

Heat exchangers are commonly used in motor vehicles as a means of transferring thermal energy between fluids. A heat exchanger may include a core having a first fluid flow path and a second fluid flow path, wherein the first fluid flow path is fluidly separated and in thermal communication with the second fluid flow path to facilitate a transfer of thermal energy therebetween. For example, the first fluid flow path may comprise a plurality of tubes or plates through which a first fluid flows, and second fluid flow path may comprise a matrix of passages which are formed intermediate to the tubes or plates of the first fluid flow path, wherein thermal energy is transferred through the walls of the tubes or plates from the first fluid to a second fluid.

Heat exchangers are generally formed of a core configured to facilitate an exchange of thermal energy with a fluid passing therethrough. A header is disposed on at least one end of the core, and provides an interface between the core and a fluid reservoir, such as a tank or manifold. One common type of header is known as a recessed header, which includes a recessed outer rim configured to receive a sealing element therein.

To ensure proper sealing between the fluid reservoir and the header, a height or thickness of the sealing element must be sufficient, wherein the sealing element will be compressed within the recessed outer rim by the fluid reservoir when the heat exchanger is assembled. It is known in the art to use a sealing element having a circular cross section. By using a sealing element with a circular cross section, a maximum height or thickness of the sealing element within the recessed outer rim is ensured. However, although functional for maintaining a fluid seal between the header and the fluid reservoir, the use of a cylindrical seal disadvantageously requires the header to have a large outer profile, as a width of the recessed outer rim must be sufficient to accommodate the width of the sealing element.

Accordingly, there exists a need in the art for an improved sealing element having a minimized width, which is configured to maintain a maximized height within a recessed outer rim of a header.

SUMMARY OF THE INVENTION

In concordance with the instant disclosure, an improved sealing element having a minimized width, which is configured to maintain a maximized height within a recessed outer rim of a header is surprisingly discovered.

In a first embodiment, a sealing element for a heat exchanger includes an elongate main body, wherein a cross section of the main body has a height and a width defining a height and a width of the main body. The height of the cross section is greater than the width of the cross section. The sealing element further includes a plurality of lugs protruding laterally from the main body. The plurality of the lugs is spaced at first predetermined intervals along a length of the main body. A height of the lugs is less than the height of the main body. The sealing element further includes a plurality of enlarged portions spaced at second predetermined intervals along the length of the main body. A height of the enlarged portions is the same as the height of the main body, and a width of the enlarged portions is greater than the width of the main body.

In another embodiment, a sealing element includes an elongate main body. A plurality of lugs are spaced at predetermined intervals along a length of the main body. A plurality of enlarged portions are spaced at second predetermined intervals along the length of the main body, wherein the plurality of the enlarged portions and the plurality of the lugs are alternatingly arranged along the length of the main body.

In yet another embodiment, a sealing element for a heat exchanger includes a first side and a second side. The first side of the sealing element has a first plurality of lugs and a plurality of enlarged portions, wherein the first plurality of the lugs and the enlarged portions are alternatingly arranged along a length of the first side. The second side of the sealing element includes a second plurality of the lugs, and does not include the enlarged portions.

DETAILED DESCRIPTION OF THE INVENTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

Figure 1:
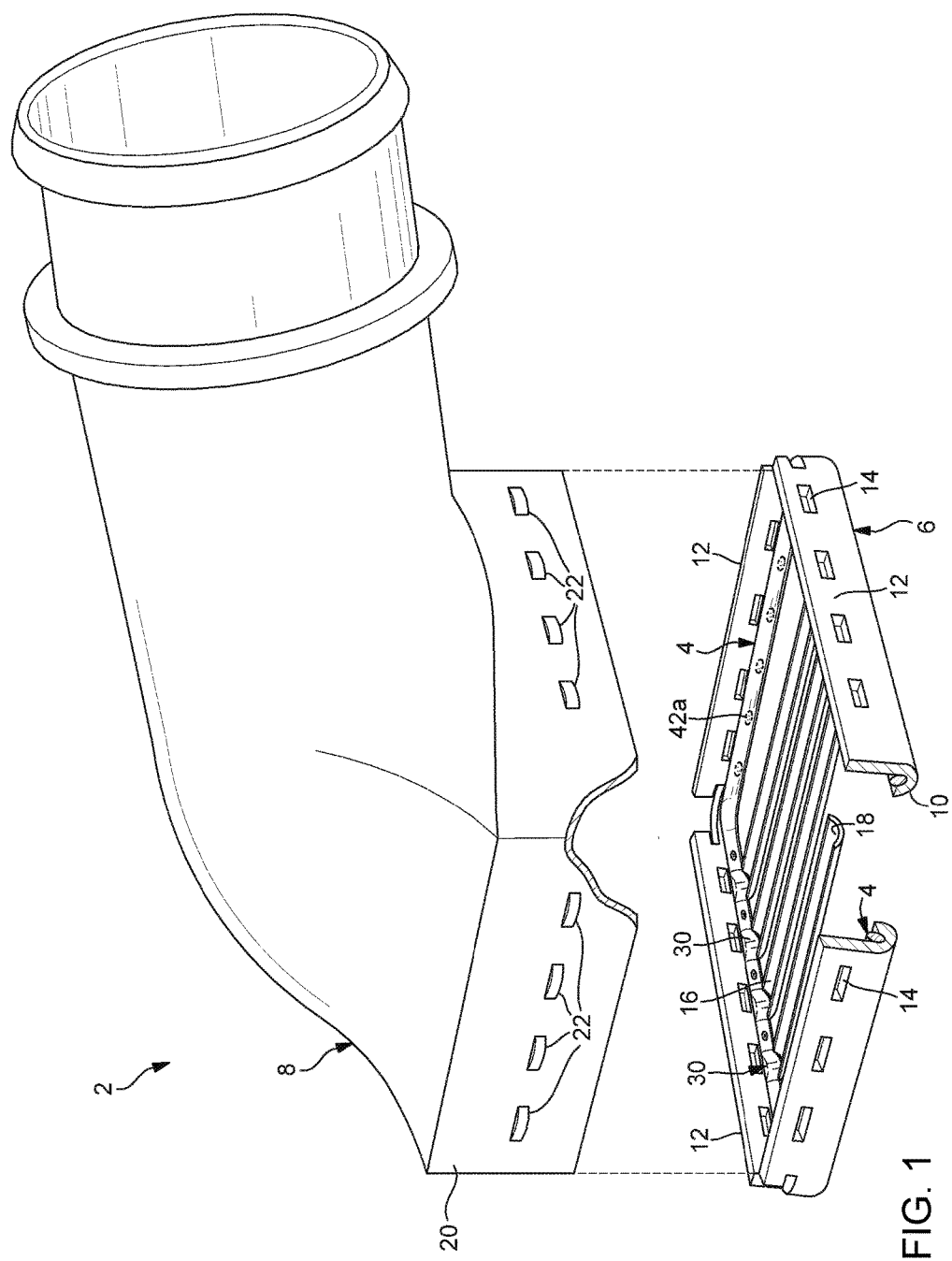
FIG. 1 is a partially exploded fragmentary top perspective view of a heat exchanger including a fluid reservoir, a header, and one embodiment of a sealing element according to the instant disclosure.

FIG. 1 shows a heat exchanger 2 having a sealing element 4 according to the instant disclosure. The heat exchanger 2 includes a header 6 configured to be coupled to an open end of a heat exchanger core (not shown), as is known in the art. The header 6 is configured to sealingly and removably couple a fluid reservoir 8 of the heat exchanger 2 to the core.

The header 6 may be coupled to the heat exchanger core using mechanical means, such as welding, crimping, and brazing, for example. Alternatively, the header 6 may be integrally formed with the heat exchanger core.

The header 6 is configured to cooperate with a portion of the fluid reservoir 8 when the heat exchanger 2 is assembled. Particularly, a recessed outer rim 10 circumscribes at least a portion of a perimeter of the header 6, and is configured to receive at least a portion of the fluid reservoir 8 therein. In alternate embodiments, a recess may be formed in the fluid reservoir 8, wherein a portion of the header 6 is received therein. In the illustrated embodiment, a plurality of mounting tabs 12 extends from the recess, wherein a single one of the mounting tabs 12 spans each of the sides of the header 6. Each of the mounting tabs 12 includes a plurality of first coupling features 14 formed therein.

Figure 2:
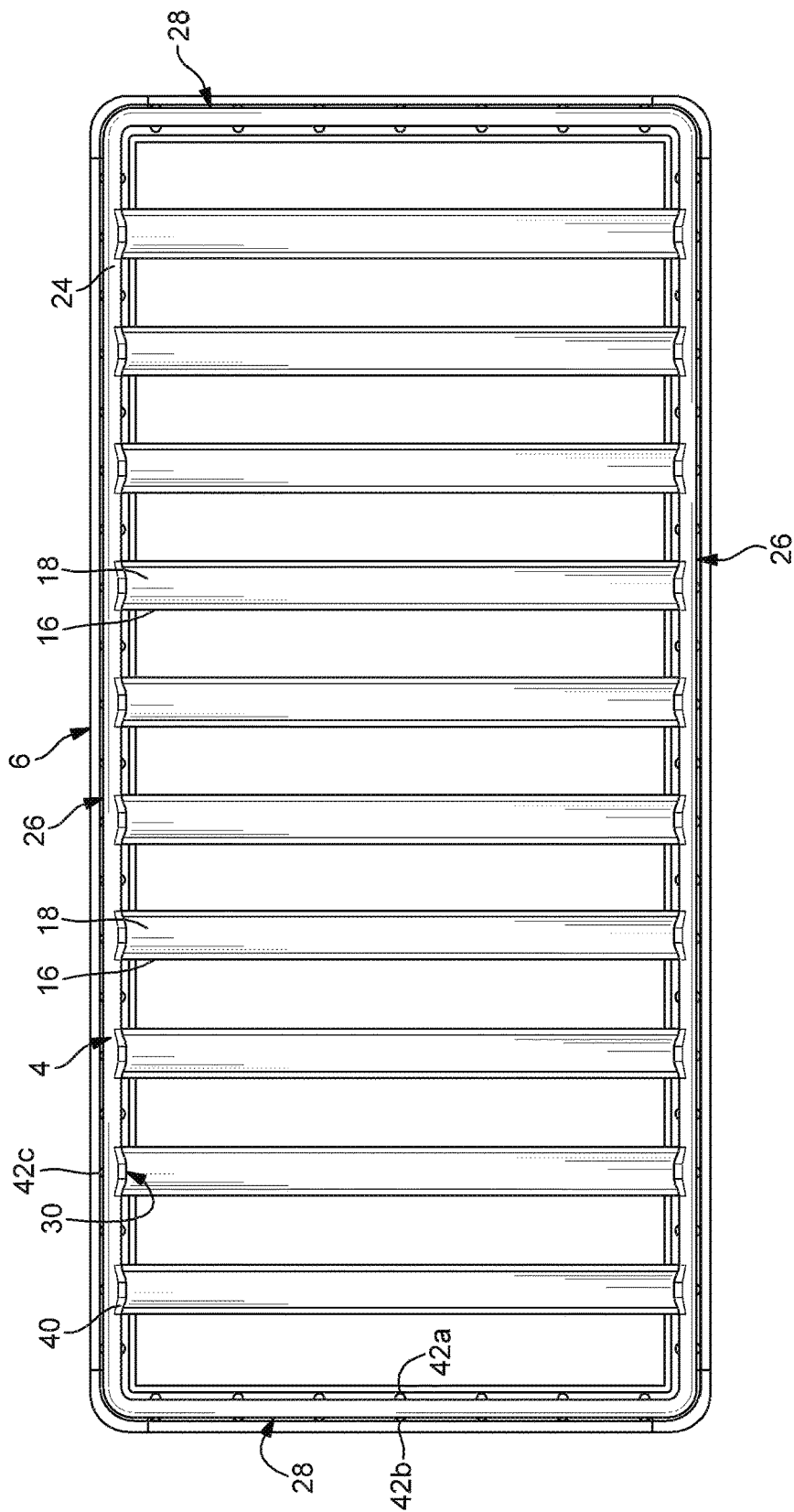
FIG. 2 is a top plan view of another embodiment of a sealing element according to the instant disclosure, wherein the sealing element is received within a header for a heat exchanger.

As shown in FIGS. 1 and 2, the header 6 further includes a plurality of crossmembers 16 spanning a distance between two opposing sides of the header 6. In the illustrated embodiment, the crossmembers 16 have a U-shaped cross section, wherein opposing ends of the crossmembers 16 terminate at an inner wall of the recessed outer rim 10 and a channel 18 defined by the U-shaped crossmember 16 is continuous with an interior of the recessed outer rim 10.

Referring again to FIG. 1, the fluid reservoir 8 includes at least one continuous sidewall 20, wherein a distal portion of the sidewall 20 is configured to be received within the recessed outer rim 10 of the header 6, thereby compressing the sealing element 4 within the recessed outer rim 10 to sealingly couple the fluid reservoir 8 and the header 6. A plurality of second coupling features 22 is spaced along the sidewall 20 of the fluid reservoir 8. In the illustrated embodiment, each of the second coupling features 22 is a protrusion extending outward from the sidewall 20, and is configured to engage a corresponding one of the first coupling features 14 of the header 6.

The sealing element 4 is disposed in the recessed outer rim 10 of the header 6. In the illustrated embodiment, the sealing element 4 is formed separately from each of the fluid reservoir 8 and header 6. Optionally, the sealing element 4 may be integrally formed with at least one of the fluid reservoir 8 and header 6. The sealing element 4 is formed of a resilient polymeric material, such as a flouroelastomer (FKM) or an ethylene propylene diene monomer (EPDM). Other suitable materials for the sealing element 4 will be appreciated by those of ordinary skill in the art.

Figure 3:
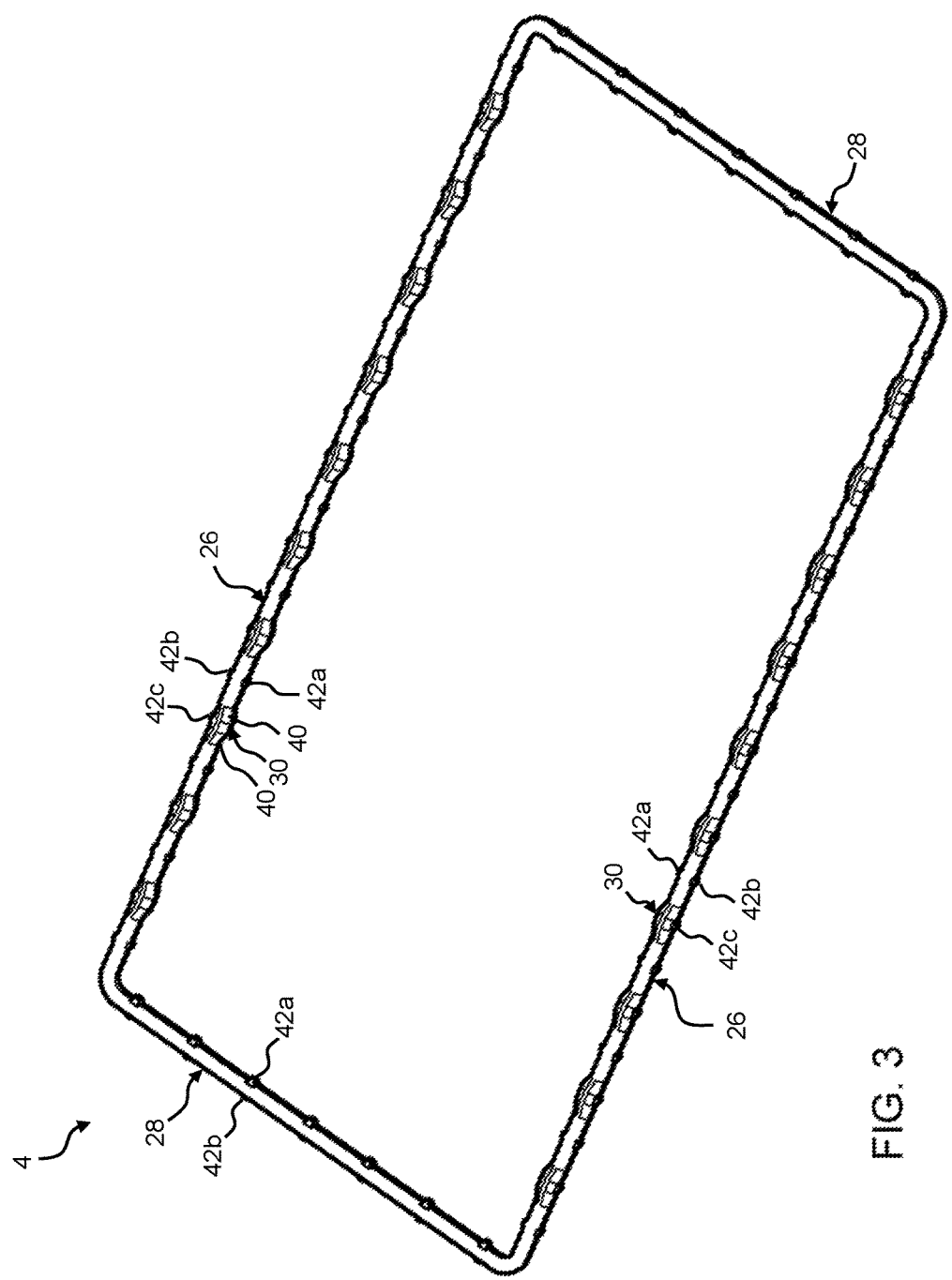
FIG. 3 is a top perspective view of the sealing element of FIG. 2.
Figure 4:
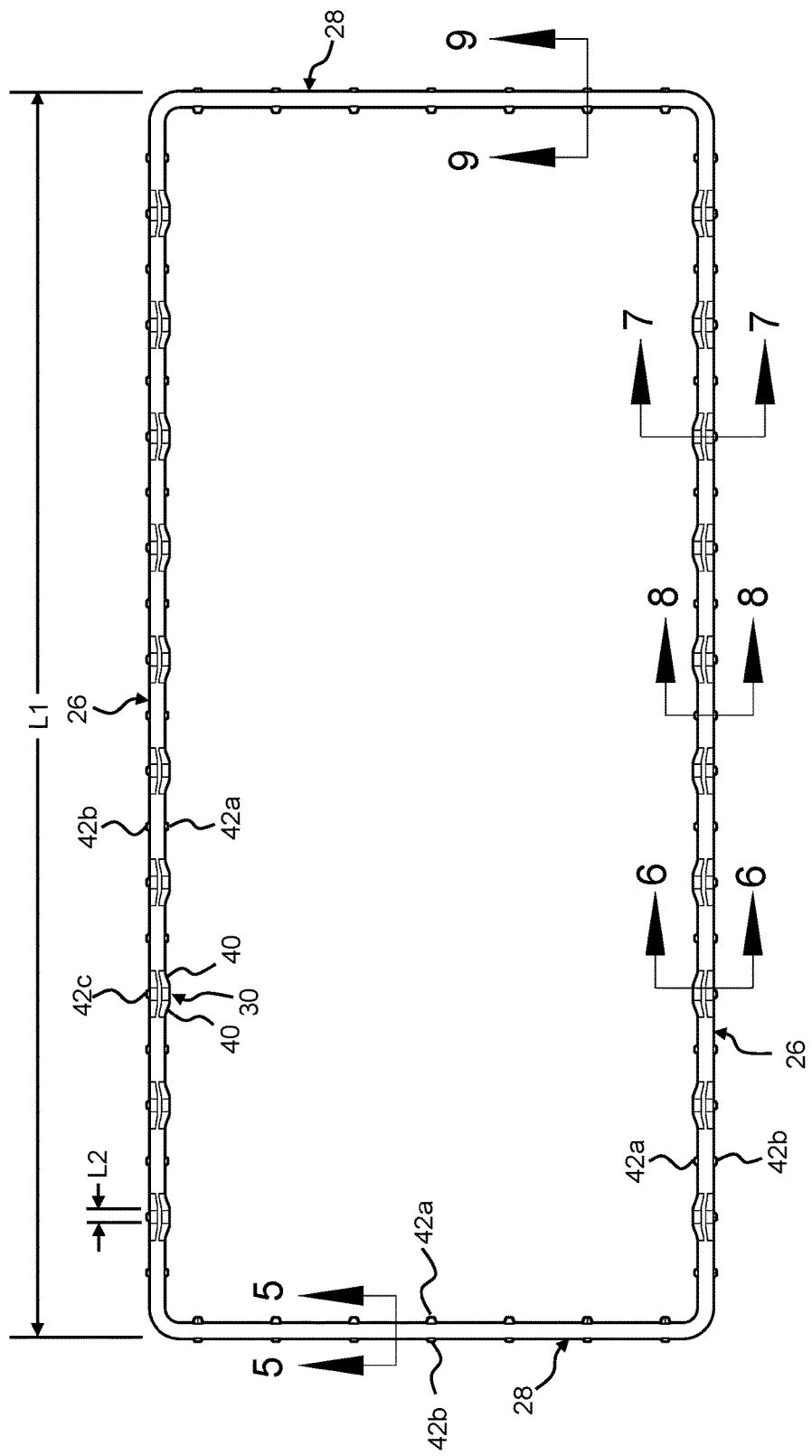
FIG. 4 is a top plan view of the sealing element of FIG. 2.
Figure 5:
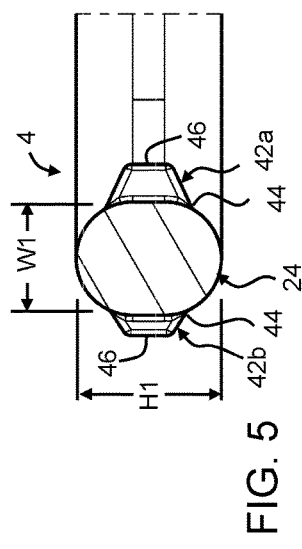
FIG. 5 is a fragmentary cross-sectional view of the sealing element of FIG. 2, taken along section line 5-5 in FIG. 4, and showing a main body of the sealing element.

As shown in FIGS. 3-5, the sealing element 4 includes an elongate main body 24. In the illustrated embodiment, the main body 24 is continuously formed and the sealing element 4 has a rectangular shape with a pair of opposing sides 26 connected to each other by a pair of opposing ends 28. As shown in FIG. 5, a cross section of the main body 24 is generally an oval or ellipse, and has a height H1 and a width W1. An aspect ratio (H1/W1) of the sealing element 4 is greater than 1:1, wherein the height H1 of the sealing element 4 is greater than the width W1. In one embodiment, the aspect ratio may range between 1:1 and 5:1, and preferably from 1.1:1 to 2:1, and more preferably be 1.3:1. The specific dimensions of the sealing element 4 are selected based on the dimensions of the recess of the header 6, wherein when the fluid reservoir 8 is received within the recess of the header 6, the seal is compressed to provide a fluid seal between the fluid reservoir 8 and the header 6.

More particularly, the cross section of the main body 24 is obround, wherein a top and a bottom of the sealing element 4 are generally semi-cylindrical in shape, and are connected by a pair of straight sidewalls. By forming the main body 24 with an obround cross-sectional shape having a semi-cylindrical top and bottom, the sealing element 4 advantageously provides a rounded compression zone similar to a purely cylindrical gasket, while simultaneously minimizing an overall profile of the sealing element 4 and the heat exchanger 2. In alternate embodiments, the cross section of the main body 24 may be polygonal or rectangular.

The sides 26 of the sealing element 4 include a plurality of enlarged portions 30 formed therein. The enlarged portions 30 are spaced at predetermined intervals along a length of each of the sides 26. The predetermined intervals correspond to a spacing between the crossmembers 16 of the header 6, wherein the enlarged portions 30 of the sealing element 4 are aligned with channels 18 of the crossmembers 16, and are configured to be partially received therein. A sum of the lengths L2 of the enlarged portions is less than one-third of a total length L1 of each of the sides 26 of the sealing element 4, as indicated in FIG. 4.

Figure 6:
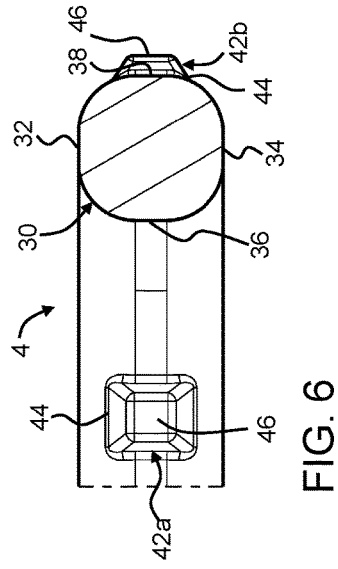
FIG. 6 is a fragmentary cross-sectional view of the sealing element of FIG. 2, taken along section line 6-6 in FIG. 4, and showing an enlarged portion of the sealing element.

A height H2 of the enlarged portion is the same as the height H1 of the main body, while a width W2 of the enlarged portion is greater than the width W1 of the main body. In one embodiment of the sealing element 4, a cross section of each of the enlarged portions 30 has an equal height H2 and width W2, wherein an aspect ratio of the cross section of the enlarged portion 30 is 1:1. The enlarged portions 30 are configured to militate against rotation of the sealing element 4 within the recess of the header 6 during compression. As shown in FIG. 6, the cross section of each of the enlarged portions 30 includes a pair of opposing horizontal sides defining a top surface 32 and a bottom surface 34 of the enlarged portion 30, and a pair of opposing vertical sides forming an inner surface 36 and an outer surface 38 of the enlarged portion 30. As shown in FIG. 6, the cross section of the enlarged portion 30 is a rounded rectangle. More particularly, the cross section of the enlarged portions 30 is a rounded square. In alternate embodiments, the enlarged portions 30 may be oblong or polygonal shapes having opposing horizontal sides, and opposing vertical sides formed intermediate the horizontal sides, and rounded corners.

Figure 8:
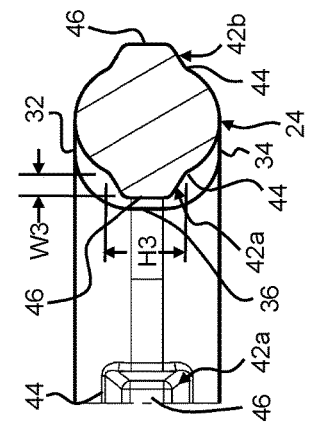
FIG. 8 is a fragmentary cross-sectional view of the sealing element of FIG. 2, taken along section line 8-8 in FIG. 4, and showing the main body and a first pair of lugs of the sealing element.

As shown in FIGS. 4 and 8, the enlarged portion 30 is offset laterally inwardly with respect to the main body 24 and the height H2 of the enlarged portion 30 is the same as the height H1 of the main body 24, wherein the top surface 32, the bottom surface 34, and the outer surface 38 of the enlarged portions 30 are formed continuously with the main body 24, and the inner surfaces 36 of the enlarged portions 30 are offset laterally inwardly from the main body 24. As shown in FIGS. 3 and 4, the enlarged portion 30 may include transitional areas 40 between the main body 24 and the inner surface 36 of the enlarged portion 30, wherein the sealing element 4 is progressively tapered between the main body 24 and the inner surface 36. By offsetting the enlarged portion 30 laterally inwardly, the width W2 of the enlarged portions 30 can be maximized without increasing a profile of the header 6, as the enlarge portion is advantageously configured to be accommodated by the channel 18 of the crossmembers 16 without increasing a width of the recess.

The sealing element 4 further includes a plurality of lugs 42 protruding laterally from the main body 24. In one embodiment, an overall height H3 of each of the lugs 42 is less than one-half of the height H1 of the main body. A width W3 of each of the lugs 42 is less than a difference between the widths W2 of the enlarged portions 30 and the width W1 of the main body 24, wherein the lugs 42 do not protrude laterally beyond the inner surfaces 36 of the enlarged portions 30.

As shown in FIGS. 5-9, each of the lugs 42 is a frustum including a base portion 44 formed adjacent the main body 24 of the sealing element 4, and a contact surface 46 extending laterally away from the main body 24 of the sealing element 4. Each of the lugs 42 may be tapered from the base portion 44 to the contact surface 46, wherein a cross-sectional area of the base portion 44 is greater than a cross-sectional area of the contact surface 46. In the illustrated embodiment, each of the lugs 42 is frusto pyramidal, wherein each of the base and the contact surface 46 are rectangular in shape. In alternate embodiments, the lugs 42 may be semi-spherical, or frusto conical, wherein each of the base and the contact surface 46 are circular.

The plurality of the lugs 42 includes pairs of the lugs 42 formed on the sides 26 and the ends 28 of the sealing element 4. Each one of the pairs of the lugs 42 includes a first lug 42a protruding laterally inwardly from the main body 24 and a second lug 42b protruding laterally outwardly from the main body 24, opposite the first lug 42a. Put another way, the first lug 42a and the second lug 42b of each of the pairs of the lugs 42 are aligned along the length of the main body 24, and extend in opposing first and second directions from each other.

First pairs of the lugs 42 are longitudinally spaced in predetermined intervals along each of the sides 26 of the sealing element 4. The first pairs of the lugs 42 are alternatingly arranged with the enlarged portions 30 of the sealing element 4, wherein one of the enlarged portions 30 is formed intermediate adjacent ones of the first pairs of the lugs 42. As shown in FIG. 8, the first lugs 42a and the second lugs 42b forming the first pairs of the lugs 42 are substantially similar in size and shape. However, in alternate embodiments, the first lugs 42a and the second lugs 42b of the first pairs of the lugs 42 may be different in size.

Figure 9:
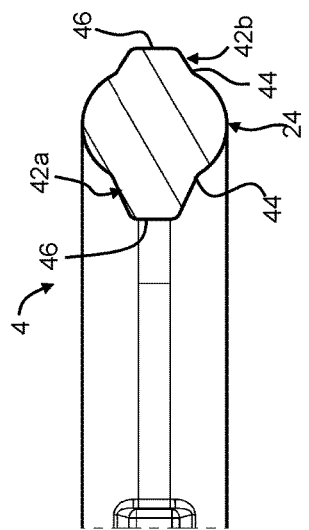
FIG. 9 is a fragmentary cross-sectional view of the sealing element of FIG. 2, taken along section line 9-9 in FIG. 4, and showing the main body and a second pair of lugs of the sealing element.

Second pairs of the lugs 42 are longitudinally spaced in predetermined intervals along each of the ends 28 of the sealing element 4. The first lugs 42a and the second lugs 42b of the second pairs of the lugs 42a, 42b are different in size, wherein first lug 42a protrudes farther from the main body 24 than the second lug 42b, as shown in FIGS. 5 and 9. In alternate embodiments, the first lugs 42a and the second lugs 42b of the second pairs of the lugs 42 may be substantially similar in size.

Figure 7:
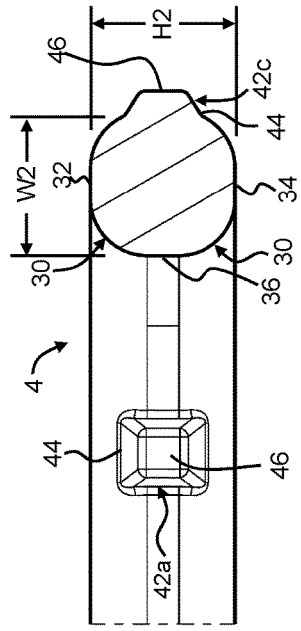
FIG. 7 is a fragmentary cross-sectional view of the sealing element of FIG. 2, taken along section line 7-7 in FIG. 4, and showing the enlarged portion and a lug of the sealing element.

As shown in FIG. 7, the sides 26 of the sealing element 4 may further include laterally outwardly protruding lugs 42c formed on the outer surface 38 of each of the enlarged portions 30. The lugs 42c formed on the enlarged portions 30 are configured to advantageously bias the enlarged portions 30 into the channels 18 of the crossmembers 16.

The use of a combination of lugs 42 and enlarged portions 30 provides an improvement over the prior art. The lugs 42 function to maintain the main body 24 of the sealing element 4 in an upright orientation within the recessed outer rim 10, wherein the sealing element 4 is maintained at a maximum height to ensure compression. The laterally offset enlarged portions 30 further provide stability to the sealing element 4 while maintaining a minimal profile of the sealing element 4.

From the foregoing description, one ordinarily skilled in the art can easily ascertain the essential characteristics of this invention and, without departing from the spirit and scope thereof, can make various changes and modifications to the invention to adapt it to various usages and conditions.

The invention claimed is:

1. A sealing element for sealing a contact surface of a header of a heat exchanger and a fluid reservoir comprising:
    an elongate main body, wherein a cross section of the main body is an oval having a height and a width defining a height and a width of the main body, the height of the cross section of the main body greater than the width of the cross section of the main body;
    lugs protruding laterally outwardly from a surface of the main body, a height of the lugs less than the height of the main body; and
    enlarged portions formed along a length of the main body, wherein a height of each of the enlarged portions is the same as the height of the main body and a width of each of the enlarged portions is greater than the width of the main body, wherein each of the enlarged portions includes one of the lugs protruding laterally outwardly therefrom.

2. The sealing element of claim 1, wherein a sum of lengths of the enlarged portions is less than one-third of a length of the sealing element.

3. The sealing element of claim 1, wherein a cross section of each of the enlarged portions is a rounded square.

4. The sealing element of claim 1, wherein each of the enlarged portions is laterally offset with respect to the main body.

5. The sealing element of claim 1, wherein a ratio of the height of the main body to the width of the main body is between 1.1 and 2.

6. The sealing element of claim 1, wherein the height of the lugs is less than one-half of the height of the main body.

7. The sealing element of claim 1, wherein a width of each of the lugs is less than a difference between the width of each of the enlarged portions and the width of the main body.

8. The sealing element of claim 1, wherein a contact surface of each of the lugs is a square.

9. The sealing element of claim 1, wherein the lugs protrude from a first side and a second side of the main body, and are arranged as opposing pairs of the lugs along the main body.

10. The sealing element of claim 1, wherein the lugs and the enlarged portions regularly alternate along a length of the main body.

11. A sealing element for a heat exchanger comprising:
    an elongate main body, wherein a cross section of the main body has a height and a width, the height greater than the width; and
    a plurality of lugs protruding laterally outwardly from a surface of the main body and spaced at first predetermined intervals along a length of the main body; and
    a plurality of enlarged portions spaced at second predetermined intervals along the length of the main body, a height of the enlarged portions the same as a width of the enlarged portions, wherein each of the plurality of the enlarged portions includes one of the plurality of the lugs protruding laterally outwardly therefrom.

12. The sealing element of claim 11, wherein the main body is continuously formed and defines a first side and a second side of the sealing element, and wherein the first side includes the plurality of the lugs and the plurality of the enlarged portions, and the second side includes only the plurality of the lugs.

13. The sealing element of claim 11, wherein the plurality of the lugs includes a plurality of pairs of the plurality of the lugs, wherein each one of the plurality of pairs of the plurality of the lugs includes a first lug laterally protruding in a first direction and a second lug protruding in an opposing second direction, wherein the second lug is longitudinally aligned with the first lug in an opposing second direction.

14. The sealing element of claim 13, wherein the plurality of pairs of the plurality of the lugs and the plurality of the enlarged portions are alternatingly arranged along the main body.

15. The sealing element of claim 11, wherein at least one of the plurality of the lugs is longitudinally aligned with at least one of the plurality of the enlarged portions of the main body.

16. A sealing element for a heat exchanger comprising:
an elongate main body;
a plurality of lugs spaced at first predetermined intervals along a length of the main body; and
a plurality of enlarged portions spaced at second predetermined intervals along the length of the main body, wherein the plurality of the enlarged portions and the plurality of the lugs are alternatingly arranged along the length of the main body, wherein each of the plurality of the enlarged portions includes one of the plurality of the lugs protruding laterally outwardly therefrom.

17. The sealing element of claim 16, wherein each of the plurality of the lugs is tapered, and wherein a cross-sectional area of a contact surface of each of the plurality of the lugs is less than a cross-sectional area of the base portion of each of the plurality of the lugs.

18. The sealing element of claim 16, wherein a height of each of the plurality of the enlarged portions is the same as a width of each of the plurality of the enlarged portions.

* * * * *